United States Patent [19]

Yabushita et al.

[11] Patent Number: 5,584,882
[45] Date of Patent: Dec. 17, 1996

[54] ANTITHROMBOTIC INTRAOCULAR LENS

[75] Inventors: Yasunori Yabushita; Munehiro Takatsuka; Shinichi Sakai, all of Kyoto, Japan

[73] Assignee: Unitika Ltd., Hyogo, Japan

[21] Appl. No.: 486,582

[22] Filed: Jun. 7, 1995

Related U.S. Application Data

[63] Continuation of Ser. No. 42,654, Apr. 2, 1993, abandoned.

[30] Foreign Application Priority Data

Apr. 3, 1992  [JP]  Japan ................................. 4-112158

[51] Int. Cl.$^6$ ....................................................... A61F 2/16
[52] U.S. Cl. .............................................................. 623/6
[58] Field of Search ........................................ 623/6, 11, 66, 623/4, 5; 351/159, 160 R, 166

[56] References Cited

U.S. PATENT DOCUMENTS

| | | |
|---|---|---|
| 4,720,512 | 1/1988 | Hu et al. . |
| 5,080,924 | 1/1992 | Kamel et al. . |
| 5,171,267 | 12/1992 | Ratner et al. ................................ 623/6 |

FOREIGN PATENT DOCUMENTS

| | | |
|---|---|---|
| 0028122 | 5/1981 | European Pat. Off. . |
| 0470474 | 7/1991 | European Pat. Off. . |
| 2257147 | 6/1993 | United Kingdom . |
| 9115952 | 10/1991 | WIPO . |

OTHER PUBLICATIONS

*Biomaterials*, vol. 10, pp. 511–516 (Oct., 1989).

*Primary Examiner*—Debra S. Brittingham
*Attorney, Agent, or Firm*—Sughrue, Mion, Zinn, Macpeak & Seas

[57] ABSTRACT

The antithrombotic intraocular lens of the present invention carries a fibrinolytic substance conjugatedly immobilized on its surface and, as such, lyses insoluble proteins such as fibrin deposited on the lens surface from the blood and exudate after implantation to fully retain its lens function. Furthermore, the present invention inhibits adhesion of the lens to the surrounding tissues and contributes to accelerated recovery after operation. The present invention further provides a simple method for immobilizing a fibrinolytic substance by conjugation on the surface of a variety of lens materials including silicones. Moreover, because the fibrinolytic substance is immobilized only to the surface of the lens material, the dynamic and optical properties of the intraocular lens are not adversely affected.

7 Claims, No Drawings

ANTITHROMBOTIC INTRAOCULAR LENS

This is a continuation of application Ser. No. 08/042,654, filed on Apr. 2, 1993, now abandoned.

FIELD OF THE INVENTION

The present invention relates to an antithrombotic intraocular lens and more particularly to an antithrombotic intraocular lens particularly suited for use in the treatment of cataracts.

BACKGROUND OF THE INVENTION

The intraocular lens is broadly used in the treatment of cataracts. The frequency of use of pseudophakos is steadily increasing with the increasing number of patients with senile cataracts; the quality of intraocular lenses (hereinafter, referred to sometimes as "IOL") has also been much improved.

However, in cases of surgery for IOL implantation, the proteins contained in the blood derived from intraoperative bleeding or in postoperative exudates may deposit on the intraocular lens, which is made of an artificial material, so that complete recovery of vision cannot be obtained in some instances. Particularly, the fibrinogen contained in the blood and exudates is activated by the IOL and the resulting insoluble fibrin not only opacifies the lens, but also favors deposition of fibroblasts and other matter on the lens surface, because of its cell adhesion property; this detracts from the designed performance characteristics of the implanted IOL.

Therefore, attempts have been made to provide intraocular lenses made of a variety of hydrophilic materials, such as, poly(2-hydroxyethyl methacrylate) (*RINGAN*, Vol. 42, No. 6pp. 618–621(June, 1988)), or to subject the IOL to surface treatment with a hydrophilic substance. However, although such materials and substances are capable of reducing the adsorption of blood-derived proteins and the like, their effect is not fully satisfactory. Moreover, even lenses made of these new materials are not completely free from the above-mentioned problems of the deposition of insoluble fibrin originating from the blood and exudates associated with the IOL implantation, and the consequent adhesion of cells to the lenses. In addition to the loss of performance due to these events, the IOL is liable to adhere to the surrounding tissues.

Also, investigations have been made to prevent the deposition of blood components by immobilizing heparin as a anticoagulant on the surface of the intraocular lens made of poly(methyl methacrylate), thereby providing a biocompatibility (*Biomaterials*, Vol. 10, pp. 511–516(Oct. 1989)). However, the heparin has an action of preventing a blood coagulation, but it suffers serious disadvantages that once fibrin is deposited from profuse bleeding and exudates, the lysis of the resulting fibrin becomes difficult.

Because of its desirable dynamic characteristics, silicone has also been used as the intraocular lens material, but because it has no effective functional groups on the surface, this material has the drawback that much time and labor are required for chemical modification on the lens surface, or other surface treatment. Furthermore, since silicone is water- and grease-repellent, such surface modifying methods tend to cause uneven coating or exfoliation of the coating, and it is difficult to cover the surface uniformly.

As a result of extensive investigation to overcome the above-mentioned conventional disadvantages, it has been found that the problems pointed out above can be neatly solved by immobilizing a substance having fibrinolytic activity on the surface of an intraocular lens. The present invention has been accomplished on the basis of the above finding.

SUMMARY OF THE INVENTION

The present invention relates to an antithrombotic intraocular lens characterized in that a substance having fibrinolytic activity has been coupled to the functional groups which are inherently present, or which are introduced onto the surface of an intraocular lens substrate to covalently immobilize the fibrinolytic substance on the surface of the intraocular lens. By virtue of the fibrinolytic substance immobilized on the surface, the intraocular lens of the present invention, when implanted, lyses deposited insoluble proteins to retain its function and inhibit its adhesion to the surrounding tissues. The present invention further provides a simple method for immobilizing a physiologically active substance on a intraocular lens substrate made of silicone which, heretofore, has been hardly conjugatable with bioactive substances.

DETAILED DESCRIPTION OF THE INVENTION

The present invention is now described in detail.

Examples of raw material for the intraocular lens of the present invention are well known, and include polymeric materials of high clarity, such as polymethacrylates, e.g., polymethyl methacrylate or poly(2-hydroxyethyl methacrylate), silicones, e.g., polydimethylsiloxane, polymethylphenylsiloxane or polymethylvinylsiloxane, polyesters, e.g., polyethylene terephthalate, etc. Preferred are materials having functional groups capable of reacting with a fibrinolytic substance on the surface. Among such functional groups, amino, carboxyl, hydroxyl, acid anhydride, and epoxy groups are particularly preferred.

The intraocular lens itself which can be used in the present invention may be prepared by any of the known, such as, a lathe-processing method which comprises cutting a lens plate as raw material into a suitable form by means of a lathe, an injection molding method which comprises subjecting a chip as raw material to an injection molding to obtain a lens, a foundry molding method which comprises pouring a prepolymer as raw material into a mold to obtain a molded polymer, and a compression molding method which comprises subjecting a raw material to compression molding in a mold.

When the polymer itself has no such functional groups, such groups may be introduced to the polymer surface. The techniques which can be used for introducing functional groups include plasma treatments, such as, glow discharge, corona discharge, etc., oxidation-reduction, or hydrolysis reactions on the polymer surface, chemical modification with an organic reagent, such as, an aminosilane coupling agent, or an organometal reagent and the like. It is also possible to introduce functional groups by the graft-polymerization of a vinyl compound having such functional groups to the polymer surface by means of γ-rays and an electron beam.

Although functional groups can be introduced by the various techniques mentioned above, a method should be selected which does not affect the optical and dynamic properties of the intraocular lens material itself by the reaction induced. Whereas other techniques are subject to some limitation or other in the compatible polymer species, plasma technology is advantageous in that functional groups can be easily introduced into most organic polymeric materials, inclusive of silicones.

The method for plasma treatment which can be used for purposes of the present invention may be any of the known methods, such as, glow discharge treatment, and corona discharge treatment. Glow discharge treatment is a surface treatment which is carried out by discharge of electricity through a gas at reduced pressure in an electron tube, or the like; while the degree of vacuum is not critical, it is preferably in the range of 10 mm to 0.01 mmHg. Corona discharge treatment is carried out at or about atmospheric pressure. The gas which can be used for such a plasma treatment is not particularly limited, it being required only that the gas be one which allows the desired functional groups to be introduced onto the substrate surface. For example, various reactive gases, such as, oxygen, nitrogen, ammonia, etc. as well as inert gases, such as, helium and argon can be employed. It is also possible to employ a mixture of two or more different gases, such as air. The gas to be used for plasma treatment varies with the kind of functional group to be introduced on the surface of the substrate polymer. For the introduction of amino groups, a gas containing atomic nitrogen, preferably ammonia gas, is employed. Although, depending on conditions, functional groups of more than one kind can be introduced as the result of plasma treatment there is no problem as long as functional groups of the intended kind can be effectively introduced. The discharge output may be selected within the capacity range of the discharge device, and is preferably in the range of 10 to 1000 W. The treatment time is also optional, but is preferably within the range of 1 second to 1 hour.

In the present invention, the fibrinolytic substance is bound to the functional groups present or introduced on the surface of the substrate intraocular lens with the aid of a compound having one or more reactive functional groups. By this method, the functional groups present or introduced on the surface of the intraocular lens substrate are caused to react with the compound having reactive functional groups and, further, this latter compound reacts with the fibrinolytic substance to form a conjugate; as a result, through this compound having reactive functional groups, the fibrinolytic substance is immobilized on the surface of the intraocular lens substrate. Alternatively, the functional groups present, or introduced on the lens substrate are caused to react with the fibrinolytic substance in the presence of the compound having reactive functional groups, whereby the fibrinolytic substance is directly immobilized on the substrate's surface.

An exemplary procedure for immobilizing the fibrinolytic substance on the surface of the lens substrate comprises reacting the lens substrate with the fibrinolytic substance in the presence of the compound having reactive functional groups in an aqueous solution, or in an organic solvent which does not dissolve the intraocular lens material. The reaction temperature is not critical, but is preferably in the range of 0° C. to 100° C.; in the case where the fibrinolytic substance is a polypeptide or protein, the reaction is preferably carried out at a temperature of 0° C. to 50° C. The reaction time is not critical, either, but is preferably in the range of 10 minutes to 48 hours.

Examples of compounds having reactive functional groups which can be used in the present invention include, inter alia, carbodiimides, such as, dicyclohexylcarbodiimide, 1-ethyl-3-(3-dimethylaminopropyl) carbodiimide hydrochloride, etc.; aldehydes, such as, glutaraldehyde, terephthalaldehyde, isophthalaldehyde, dialdehyde starch, etc.; isocyanates, such as, hexamethylene diisocyanate, tolylene diisocyanate, xylylene diisocyanate, phenylene diisocyanate, etc.; acid chlorides, such as, adipoyl chloride, isophthaloyl chloride, terephthaloyl chloride, cyanuric chloride, etc.; polythiocyanates, such as, hexamethylene thiocyanate etc.; N,N'-polymethylenebisiodoacetamide such as N,N'-ethylenebisiodoacetamide, N,N'hexamethylenebisiodoacetamide, etc.; polyepoxides, such as, tetramethylene glycol diglycidyl ether, diethylene glycol diglycidyl ether, etc.; polycarboxylic anhydride, such as, maleic anhydride-methyl vinyl ether copolymer, maleic anhydride-ethylene copolymer, maleic anhydride-styrene copolymer, etc.; bismaleimides, such as, N,N'-ethylenebismaleimide etc.; poly(meth)acryloyl compounds, such as, N,N'-methylenebis(meth)acrylamide, N,N'-hexa-methylenebis(meth)acrylamide, N,N',N''-triacryloylhexa-hydrotriazine, etc.

The fibrinolytic substance, which can be employed for purposes of the present invention, is any substance that, among substances associated with the blood coagulation fibrinolysis system, lyses insoluble fibrin which is a major constituent of a thrombus, and includes, inter alia, urokinase, streptokinase, tissue plasminogen activator (TPA), brinolase, plasmin, phenylbutazone, mefenamic acid and indomethacin.

The present invention is now illustrated in greater detail with reference to the following examples, but it should be understood that the present invention is not deemed to be limited thereto.

EXAMPLE 1

A silicone intraocular lens, 5 mm in diameter and 2 mm in thickness, was placed in a plasma reactor (PR-501A, manufactured by Yamato Kagaku); at an output setting of 300W, the lens was plasma-treated in the presence of ammonia gas for 10 minutes. The treated silicone lens was then immersed in a 1% (w/w) solution of maleic anhydride-methyl vinyl ethyl copolymer in acetone for 1 hour, after which it was taken out and washed with acetone. This intraocular lens was further immersed in an aqueous solution of urokinase (1000 IU/ml) at room temperature for 24 hours, rinsed with deionized water, and dried, under reduced pressure, to provide an urokinase-immobilized intraocular lens.

The urokinase activity of this intraocular lens was measured by the synthetic substrate method (Morita et al., J. Biochem., 82, 1495(1977)). It was confirmed that 43.7 IU/cm$^2$ of urokinase had been immobilized on the lens surface.

Further, the fibrinolytic activity of this intraocular lens was assayed by reference to the method of Kanai et al. [Rinsho Kensa-ho Teiyo (Handbook of Laboratory Tests), 27th revised edition, Kinbara Publishing Co., VI-100]. Thus, the urokinase-immobilized intraocular lens was placed on a fibrin membrane and incubated at 37° C. for 24 hours. Then, the image of lysis of the fibrin was examined. Furthermore, the same intraocular lens was washed with deionized water, and placed on another fresh fibrin membrane for re-lysis. This procedure was repeated. As a result, lysis of fibrin was still observed, even after 5 runs.

EXAMPLE 2

A lens substrate, similar to that of Example 1, was treated in the same manner as in Example 1, except that 0.1 mg/ml of streptokinase was used in lieu of urokinase to provide a streptokinase-immobilized intraocular lens.

The fibrinolytic activity of this intraocular lens was assayed in the same manner as in Example 1. As a result, it was confirmed that lysis of fibrin membranes was accomplished to a similar extent as in Example 1.

EXAMPLE 3

A polymethyl methacrylate intraocular lens, 5 mm in diameter and 2 mm in thickness, was placed in a plasma reactor (PR-501A, manufactured by Yamato Kagaku); using an output setting of 300 W, the lens was plasma-treated in the presence of oxygen gas for 2 minutes. This intraocular lens was then immersed in an aqueous solution of 1-ethyl-3-(3-dimethylaminopropyl) carbodiimide hydrochloride (10 mg/ml) at 4° C. for 30 minutes. Then, 1000 IU/ml of urokinase solution was added and the system was stirred for 24 hours. The intraocular lens was then taken out, rinsed with deionized water, and dried, under reduced pressure, to provide an urokinase-immobilized intraocular lens.

The urokinase activity of this intraocular lens was measured in the same manner as in Example 1. As a result, it was confirmed that 18.4 IU/cm$^2$ of urokinase had been immobilized on the lens surface.

Further, the fibrinolytic activity of this lens was assayed in the same manner as in Example 1. As a result, it was confirmed that lysis of fibrin membranes was accomplished to a similar extent as in Example 1.

EXAMPLE 4

A polymethyl methacrylate intraocular lens, 5 mm in diameter and 2 mm in thickness, was immersed in 0.5 N sodium hydroxide solution and boiled for 30 minutes. After spontaneous cooling, the lens was neutralized in 0.01 N hydrochloric acid, and then rinsed with deionized water to provide a surface-hydrolyzed polymethyl methacrylate lens. This lens was immersed in an aqueous solution of 1-ethyl-3-(3-dimethylaminopropyl) carbodiimide hydrochloride (10 mg/ml) at 4° C. for 30 minutes, at the end of which time 1000 IU/ml of urokinase was added. The system was then stirred for 24 hours. The intraocular lens was taken out, rinsed with deionized water, and dried, under reduced pressure, to provide an urokinase-immobilized intraocular lens.

The urokinase activity of this intraocular lens was measured in the same manner as in Example 1. As a result, it was confirmed that 15.3 IU/cm$^2$ of urokinase had been immobilized on the lens surface.

Further, the fibrinolytic activity of this lens was assayed in the same manner as in Example 1. As a result, it was confirmed that lysis of fibrin membranes was accomplished to a similar extent as in Example 1.

While the invention has been described in detail and with reference to specific embodiments thereof, it will be apparent to one skilled in the art that various changes and modifications can be made therein without departing from the spirit and scope thereof.

What is claimed is:

1. An antithrombotic intraocular lens consisting essentially of an intraocular lens having an active fibrinolytic substance immobilized thereon, wherein said intraocular lens consists essentially of a polymeric material comprising functional groups covalently bound thereon, and wherein said active fibrinolytic substance is directly immobilized on said lens by covalent bonding of said active fibrinolytic substance to said functional groups, and said active fibrinolytic substance is selected from the group consisting of urokinase, streptokinase, tissue plasminogen activator, brinolase, plasmin, phenylbutazone, mefenamic acid and indomethacin.

2. The antithrombotic intraocular lens of claim 1, wherein said functional groups are naturally present on said polymeric material.

3. The antithrombotic intraocular lens of claim 1, wherein said polymeric material has been chemically treated to introduce said functional groups.

4. The antithrombotic intraocular lens of claim 1, wherein said polymeric material is a silicone material.

5. The antithrombotic intraocular lens of claim 3, wherein said polymeric material is a silicone material.

6. The antithrombotic intraocular lens of claim 1, wherein said functional groups are introduced onto said polymeric material by plasma treatment.

7. The antithrombotic intraocular lens of claim 6, wherein said polymeric material is silicone, and said functional groups are introduced onto said silicone by plasma treatment.

* * * * *